United States Patent [19]

Pez et al.

[11] 4,268,454
[45] May 19, 1981

[54] ANIONIC GROUP VIII METAL HYDRIDE CATALYSTS

[75] Inventors: Guido P. Pez, Boonton; Roger A. Grey, Denville, both of N.J.

[73] Assignee: Allied Chemical Corporation, Morris Township, Morris County, N.J.

[21] Appl. No.: 70,583

[22] Filed: Aug. 29, 1979

Related U.S. Application Data

[63] Continuation-in-part of Ser. No. 972,147, Dec. 21, 1978, abandoned.

[51] Int. Cl.$^3$ .................... C07F 15/02; C07F 15/00
[52] U.S. Cl. ................. 260/439 R; 252/431 P; 260/429 R; 568/861; 568/880; 585/275; 585/277
[58] Field of Search ................. 260/429 R, 439 R

[56] References Cited

U.S. PATENT DOCUMENTS

| | | | |
|---|---|---|---|
| 3,133,943 | 5/1964 | Chatt et al. ............... | 260/429 R |
| 3,418,303 | 12/1968 | Barney et al. ............ | 260/429 R X |
| 3,878,122 | 4/1975 | Pennella .................. | 260/429 R X |
| 4,013,583 | 3/1977 | Knifton ................... | 260/429 R X |

FOREIGN PATENT DOCUMENTS

1246123  9/1971  United Kingdom ............ 260/429 R

OTHER PUBLICATIONS

Roundhill, Adv. in Organometallic Chemistry Academic Press, N.Y. V. 13 pp. 343–353 (1975).
Chatt et al., J. Chem. Soc. 843 (1965).
Stephenson et al., Inorg. Nucl. Chem. Letters V. 7(9) pp. 805–809 (1971).
Chatt et al., J. Chem. Soc. p. 5504 (1961).
Cash et al., Can. J. Chem. 49 (23) p. 3821 (1971).
J. Organometallic Chem. V. 75, pp. 381–385 (1974).
Stephenson, J. Chem. Soc. (A) p. 889 (1970).
Cleare et al., J. Chem. Soc. (A) p. 372 (1969).
Raspin, J. Chem. Soc. p. 461 (1969).

*Primary Examiner*—Helen M. S. Sneed
*Attorney, Agent, or Firm*—Robert A. Harman; Alan M. Doernberg

[57] ABSTRACT

A novel class of compounds, anionic Group VIII metal hydrides containing phosphorus, arsenic and antimony organoligands is described, such as potassium tris and bis(triphenylphosphine) ruthenium hydride. The compounds are useful as homogeneous catalysts in the hydrogenation of aldehydes, ketones, olefins or alkynes. Processes for producing the compounds are also described.

11 Claims, No Drawings

ANIONIC GROUP VIII METAL HYDRIDE CATALYSTS

CROSS REFERENCE TO RELATED APPLICATIONS

This application is a continuation-in-part of U.S. Ser. No. 972,147, filed Dec. 21, 1978, now abandoned.

BACKGROUND OF THE INVENTION

1. Field of the Invention

This invention relates to novel anionic Group VIII metal hydrides, containing organoligands of the Group V elements of phosphorus, arsenic and antimony, and methods for their preparation, said hydrides being useful as catalysts for the hydrogenation of aldehydes, ketones, olefins and alkynes.

2. Brief Description of the Background of the Invention Including Prior Art

Main group metallic hydrides, such as lithium aluminium hydride, are well known in the art as excellent reagents for the reduction of a wide variety of unsaturated polar organic substrates such as aldehydes, ketones, carboxylic acid esters and nitriles. The disadvantage of these reagents is that they must be used in at least a stoichiometric quantity to insure high yields of desired products.

Neutral transition metal hydride complexes, such as tris (triphenylphosphine)ruthenium hydridochloride, are known to be useful in catalytic quantities for the hydrogenation of olefins, as described in J. Chem. Soc. (A) 3143 (1968) and for the oligomerization of ethylene and butadiene as described in J. Catalysis 27, 442 (1972).

A variety of metal hydride type compositions which would be able to function in catalytic quantities in the presence of gaseous hydrogen, are increasingly desired in the art for the catalyzed hydrogenation of a wide variety of unsaturated organic compounds such as aldehydes, ketones, olefins, alkynes and the like. The use of such catalysts would significantly reduce the cost of reduction reactions since the use of gaseous hydrogen in stoichiometric quantities and the use of a metal hydride in catalytic quantities would be relatively inexpensive as compared to the use of main group metallic hydrides in stoichiometric quantities.

Several anionic transition metal hydride complexes, containing specifically carbonyl ligands, are known, as for example, $Na^+HFe(CO)_4^-$ and $[V(CO)_5PPh_3]^- [Et_4N]^+$, described in J. Organomet. Chem. 31, 239 (1971).

Anionic Group VIII metal complex hydrides, containing only ligands of Group V elements, and not carbonyl ligands attached to the metal atom in the molecule, are not well known in the art.

The reference, J. Chem. Soc., 843 (1965) describes the preparation of a ruthenium complex in anionic form, namely, sodium bis(bis-dimethylphosphinoethane) ruthenium hydride, $Na[RuH(Me_2PCH_2CH_2PMe_2)_2]$ which contains four coordinated phosphorus atoms per ruthenium atom. However, the compound was not isolated or characterized and no specific mention is made of its possible usefulness as a catalyst in hydrogenation reactions, i.e. reduction by molecular hydrogen.

The reference, Chemical Communications, pp 857858 (1968), describes the preparation of specifically the ninecoordinate octahydrido(tertiaryphosphine) complex of the Group VII metal rhenium. No specific mention is made of its possible usefulness as a catalyst.

SUMMARY OF THE INVENTION

We have unexpectedly found that anionic Group VIII metal hydride complexes, having ligands containing phosphorus, arsenic or antimony atoms, in an amount of 1 to 3 of said atoms per Group VIII metal atom, and being non-carbonyl ligands, are useful as catalysts in the homogeneous hydrogenation of aldehydes, ketones, olefins and alkynes. The cationic portion of the complex can be an alkali metal cation, alkaline earth metal cation, and the like. Particularly preferred anionic Group VIII metal hydride complexes of the invention are of the following formulas:

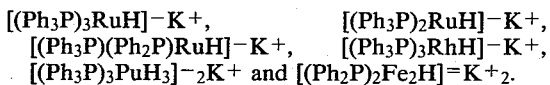

The compositions are readily soluble in conventional solvents used for hydrogenation reactions including ethers, such as tetrahydrofuran.

The anionic Group VIII metal hydride complexes can be prepared by reacting a neutral Group VIII metal complex, or adduct thereof, with a Group IA metal cationradical anion complex, hereinafter referred to as "metal arene," such as potassium naphthalene, in a solvent therefor, such as tetrahydrofuran or diethylether, at a temperature of about $-111°$ C. to $+80°$ C., under a dry inert atmosphere. The product is easily isolated and purified from the reaction mixture.

The anionic Group VIII metal hydride complexes can also be prepared by reacting a neutral Group VIII metal complex, or adduct thereof, with a Group IA metal hydride, such as potassium hydride, in a solvent therefor, such as tetrahydrofuran or diethyl ether, at a temperature of $-20°$ to $+150°$ C., under a dry inert atmosphere. The product is easily isolated and purified from the reaction mixture.

In accordance with this invention there is provided a composition of the formula:

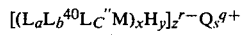

including dimers, trimers and tetramers thereof, wherein L, L' and L" are independently selected from organo-ligands containing phosphorus, arsenic or antimony elements, each ligand being a non-carbonyl ligand and containing at least one said element, M being a Group VIII metal, H being hydrido, Q being a cation, wherein a, b and c are integer values of 0 or 1, the sum of a, b and c being of from 1 to 3, x being a value of 1 or 2, y being an integer value of from 1 to 3x, x being defined as above, r and s independently being integer values of 1 or 2, and z and q independently being integer values of from 1 to 3, wherein said composition is electrically neutral and contains a minimum of one and a maximum of three atoms of phosphorus, arsenic, antimony or mixtures thereof, per Group VIII metal atom. A bidentate ligand is considered as being one ligand in the above formula even though there are two points of attachment per metal atom.

Further provided is in a process for preparing the subject composition, described above, the step of contacting a solution comprised of a metal complex of the formula: $L_aL_b'L_c''MH_mX_n$, or adduct thereof, wherein $L_a$, $L_b'$, $L_c''$ and M are defined as above, H being hydrido, X being halide, m being an integer value of from 0 to 3 and n being an integer value of from 0 to 3, in an inert solvent therefor, with a solution of Group IA metal arene, T Ar, wherein T is a Group IA metal and Ar is an aromatic moiety containing 6 to 14 carbon atoms, in an inert solvent therefor, under a dry inert atmosphere, at a temperature from about $-111°$ C. to $+80°$ C., wherein the Group IA metal arene is present in an initial amount of at least about $n+1$ equivalents per equivalent of halide in the metal complex desired to be replaced, n being defined as above, thereby resulting in the subject composition wherein cation Q is a Group IA metal. A specific embodiment is wherein said resulting composition is contacted with a salt, soluble in said solvent for the resulting composition, said salt containing cation Q being other than a Group IA metal, as defined for the subject compositions, wherein cationic exchange occurs thereby resulting in the subject composition, containing cation Q being other than a Group IA metal as defined above.

In addition there is provided in a process for preparing the subject composition the step of contacting a solution comprised of a metal complex of the formula: $L_aL_b'L_c''MH_mX_n$, or adduct thereof, wherein $L_a$, $L_b'$, $L_c''$ and M are defined as in claim 1, H being hydrido, X being halide, m being an integer value of from 0 to 3 and n being an integer value of from 0 to 3, in an inert solvent therefor, with a solution of Group IA metal hydride in an inert solvent therefor, under a dry inert atmosphere, at a temperature from about $-20°$ C. to $+150°$ C., wherein the Group IA metal hydride is present in an initial amount of at least about $n+1$ equivalents per equivalent of halide in the metal complex desired to be replaced, n being defined as above, thereby resulting in the subject composition wherein cation Q is a Group IA metal.

Also provided are improved processes for hydrogenating an aldehyde group to a primary alcohol group, a ketone group to a secondary alcohol group, an ethylenic bond to a saturated aliphatic bond, and an acetylenic bond to an ethylenic bond or saturated aliphatic bond, or mixtures thereof, in a chemical compound, respectively, including contacting a solution of hydrogenation catalyst and the respective compound, neat or in an inert solvent therefor, with an atmosphere containing hydrogen gas; the improvement which comprises providing the subject composition described hereinabove as said catalyst.

DESCRIPTION OF THE INVENTION AND PREFERRED EMBODIMENTS

The Group VIII metals present in the subject compositions include iron, cobalt, nickel, ruthenium, rhodium, palladium, osmium, iridium and platinum and preferably ruthenium, rhodium and iron.

Organoligands, independently designated as L, L' and L", present in the subject compositions include the coordinating elements: phosphorus, arsenic and antimony and preferably those of phosphorus. The number of ligands present is 1 to 3 per Group VIII metal atom, designated by the sum of a, b and c, and the value of x, and contains at least one P, As or Sb element, and included in the total number of ligands, is a maximum of three atoms of said elements present per Group VIII metal atom in the molecule. A maximum of three atoms of P, As or Sb, or mixtures thereof, per Group VIII metal atom is a limitation because it is believed that more than this number interferes in the catalytic process. For example, it has been found by us that when the anionic tris (triphenylphosphine)ruthenium complex, is employed during the homogeneous catalytic hydrogenation of ketones, additional triphenylphosphine has an adverse effect upon catalytic reactivity, wherein we believe the anionic tetrakis(triphenylphosphine)ruthenium complex is formed under the conditions.

It is also considered that carbonyl ligands generally withdraw electronic charge from the respective metal atom, to which they are attached, thus rendering any hydride ligand attached to the metal atom less hydridic in character. Since it is considered that the effectiveness of the subject compositions as homogeneous catalysts is a function of the hydridic nature of the hydride ligands, the subject compositions do not contain carbonyl ligands.

Included among the ligands applicable in the subject compositions are those designated as L, L' and L" are independently of the formulae:

$(R'R''G_1)$, $(R'R''R'''G_1)$ or
$(R'R''G_1-R-G_2R'''R'''')$, wherein $G_1$ and $G_2$ are independently phosphorus, arsenic, or antimony, R', R", R''' and R'''' are independently selected from $C_1$–$C_{18}$ linear or branched alkyl, phenyl, $C_1$–$C_{18}$ linear or branched alkylphenyl and phenylsubstituted $C_1$–$C_{18}$ alkyl, and R being a $C_1$–$C_4$ divalent alkyl bridging group between $G_1$ and $G_2$, wherein said alkyl and phenyl radicals can also be substituted with groups inert toward metal arenes, such as $C_1$–$C_4$ alkoxy, being linear or branched and the like. Bidentate ligands are considered as being one ligand in the above-described formula for the subject compositions and may form two points of attachment per Group VIII metal atom, or be bridged between two Group VIII metal atoms.

Representative examples of organoligands applicable in the invention compositions (Ph being used hereinafter to designate phenyl) are triphenylphosphine ($Ph_3P$), diphenylmethylphosphine ($Ph_2CH_3P$), diphenylphosphide ($Ph_2P$), triphenylarsine ($Ph_3As$), diphenylmethylarsine, ($Ph_2CH_3As$), trimethylphosphine, triethylphosphine, tri-n-octadecylphosphine, tri-n-octylphosphine, triisopropylphosphine, trisecondary-butylphosphine, tricyclohexylphosphine, tri(pentamethylphenyl)phosphine, tri(p-tolyl)phosphine, tri(p-noctadecylphenyl)phosphine, tri(p-n-octylphenyl)phosphine, tri(2-phenethyl)phosphine, tri-benzylphosphine, tri(2-phenylisooctadecyl)phosphine, tri(p-methoxyphenyl)phosphine, tri(2-methoxyethyl)phosphine, tri(p-tertiary-butoxyphenyl)phosphine, triphenylstibine, bis 1,2-(dimethylphosphino)ethane, ($Me_2PCH_2CH_2PMe_2$) and bis 1,2-(diphenylphosphino)ethane, ($Ph_2PCH_2CH_2PPh_2$).

Preferred ligands are those of organophosphorus and organoarsine types and more preferred are those of organophosphorus, particularly triphenylphosphine, diphenylmethylphosphine and diphenylphosphide.

The charge of the anion in the subject compositions designated by r, can be $-1$ or $-2$, and the number of anions in the composition, designated by z, can be from 1 to 3.

Cation Q in the subject compositions has a positive charge, designated by q, of from $+1$ to $+3$ and the subject composition can have from 1 to 3 cations, designated by s. Representative examples of cations applicable in the invention include the Group IA alkali metals, such as Li, Na, K, Rb and Cs, the Group IIA alkaline earth metals, such as Be, Mg, Ca, Ba and Sr, Group IIIA metals such as Al, and Ga, divalent and trivalent lanthanide elements such as $La^{+3}$ and $Eu^{+2}$, "metallocene" sandwich-type organo-metallic gegencations, such as $(C_5H_5)_2Ti^+$, and $(C_5H_5)_2V^+$, and divalent cations of transition metals such as V, Cu, Mn and Fe. Preferred cations in the compositions are $K^+$, $Li^+$, $La^{+3}$ and $V^{+2}$.

The total cationic and anionic charges in the subject compositions are equivalent in absolute value such that the resulting composition is electrically neutral.

The number of hydrogen atoms, also termed herein as "hydride or hydrido ligands", attached to the Group VIII metal atoms in the composition is from 1 to 3×, designated by the symbol y, and can be from 1 to 6, and preferably two, three or four. It is believed that where one hydrogen atom is present per two Group VIII metal atoms, the hydrogen atom is bridged between the two respective metal atoms. Preferably one of the hydride ligands present is formed by an ortho-metallation process as described below. The number of hydride ligands is easily established in the molecule by the well known technique of reacting one gram-mole of said composition in a pure state with at least about one gram-mole of hydrogen chloride, producing about one gram-mole of hydrogen gas per gramatom of hydride ligand present in the composition. Stoichiometrically, the reaction requires one grammole of hydrogen chloride, but in practice, a slight excess over this amount is used to insure complete reaction.

Representative examples of subject compositions are illustrated by the following formulas, which are approximate structural formulas, as regarded by us, on the basis of present available evidence:

$[(Ph_3P)_3RuH]^-K^+$; $[(Ph_3P)(Ph_2P)RuH]^-K^+$;
$[(Ph_3P)_2RuH]^-K^+$; $[(Ph_2P)_2FeH]^=K_2^+$;
$[(Ph_3P)_3RuH]^-Na^+$; $[(Ph_3P)_3RuH]^-Li^+$;
$[(Ph_3P)_3RuH]_2^-Mg^{+2}$; $[(Ph_3P)_2RuH]^-Li^+$;
$[(Ph_3P)_2RuH]^-Cs^+$; $[(Ph_2CH_3)_3RuH]^-K^+$;
$[(Ph_3P)_2PtH]^-K^+$; $[(Ph_3P)_3RhH]^-K^+$;
$[(PPh_3)_2Rh]_2H^-K^+$; $[(Ph_3P)_2RuH_2]^-K^+$;
$[(Ph_3P)_2RuH_3]^-K^+$ and $[(Ph_3P)_3RuH_3]^-2K^+$. The symbol Ph is used herein to designate phenyl.

Preferred subject compositions are listed below giving their approximate structural formulas, assigned Roman numerals, used herein for convenience and chemical names.

| Formula | Roman Numeral | Chemical Name |
|---|---|---|
| $[(Ph_3P)_3RuH]^-K^+$ | I | potassium tris(triphenylphosphine) ruthenium hydride |
| $[(Ph_3P)(Ph_2P)RuH]^-K^+$ | II | potassium triphenylphosphine-diphenylphosphide ruthenium hydride. |
| $[(Ph_3P)_2RuH]^-K^+$ | III | potassium bis(triphenyl phosphine) ruthenium hydride |
| $[(Ph_2P)_2FeH]^=K_2^+$ | IV | dipotassium bis(diphenylphosphide) iron hydride |
| $[(Ph_3P)_3RuH_3]_2^-K^+$ | V | potassium bis[tris(triphenylphosphine)ruthenium trihydride] |
| $[(Ph_3P)_2Rh]_2H^-K^+$ | VI | potassium bis[bis(triphenylphosphine)rhodium] hydride |

The molecular structure of the subject compositions are fairly complex and have only been rigorously studied in detail in a few cases. For example, structure (I) behaves chemically as a dihydride and, on the basis of its infrared and nuclear magnetic resonance spectra and chemical properties, can be more properly represented as being ortho-metallated by the formula:

$[(Ph_3P)_2(Ph_2PC_6H_4)RuH_2]^-K^+$.

In the case of compound (II) it is felt that orthometallation occurs, but it is not shown in the formula since it is not known which specific phosphine (or phosphide) moiety is in fact ortho-metallated. We have shown that on the basis of chemical reactivity that the compound is a dihydride and also on the basis of proton and 31p nuclear magnetic resonance spectra that the compound is a dimer. Thus, for purposes of this disclosure the following approximate structural formulas are considered to be equivalent:

$[(Ph_3P)_2(Ph_2P)_2Ru_2H_4]^=K_2^+$;
$[(Ph_3P)(Ph_2P)RuH_2]_2^-K_2^+$;
$[(Ph_3P)(Ph_2P)RuH]_2^-K_2^+$; and
$[(Ph_3P)(Ph_2P)RuH]^-K^+$.

It is also believed that other subject compositions can also exist in dimer, trimer and tetramer forms of their basic empirical formulas.

It is not clearly understood, but it is felt that the subject compositions possess the ability to undergo "ortho-metallation", a process whereby an "unfilled" coordination site on the Group VIII metal atom becomes attached by substitution onto the "ortho" position of a neighboring phenyl radical as present in triphenylphosphine. The bond formation between the metal atom and the ortho carbon on the phenyl ring displaces the ortho hydrogen atom, which then attaches to the metal atom, thus forming a dihydride, as indicated by the horizontal bracket in the above-described formula. In addition, ortho-metallation can give rise to an anionic metal hydride even when there is no hydride in the starting metal complex, i.e., m=0. It is considered that "ortho-metallation" in solution, is a dynamic, reversible process in which the orthometallated material can react back to the non-orthometallated form. This ortho-metallation behaviour may be present in the other subject compositions and can be observed by a dihydride behavior of the pure substance in that one gram-atom of hydride ligand in the subject composition will liberate one gram-mole of hydrogen gas upon reaction with at least about one gram-mole of hydrogen chloride.

Other chemical characteristics of the subject compositions are that one gram-atom of hydride ligand in the subject composition will liberate one gram-mole of methane upon reaction with at least one gram-mole of methyl iodide.

The infrared spectra of the subject compositions exhibit metal-hydride absorption maxima in the infrared region of about 1600 to 2000 $cm^{-1}$ and usually about 1750 to 1950 $cm^{-1}$.

The subject compositions can exist in the "free form" as described by the empirical formula, and also may exist wherein the cation is complexed with an organic solvent, in adduct form, or as a complex with a chelating agent for said cation. For example, structure (I) can exist as an etherate, being complexed with one mole diethylether per mole of composition. The composition can also for adducts with aromatic hydrocarbons, such as naphthalene, toluene, and chelates with chelating agents, such as crown ethers, e.g. 18-crown-6, cryptates, being bicyclic-nitrogen bridged diamines having oxyethylene bridges, such as 2.2.2-crypt, and the like. Usually the solvent adduct is present due to the inability to easily and conveniently remove the remaining solvent. The adduct, in some cases, displays better crystalline properties than the free form composition itself. In addition, there may be marked differences in the catalytic reactivity between the free form and the adduct form due to ion-pairing phenomena in solution resulting from the influence of the chelating agent upon the nature of the cation. For purposes of this invention, the scope of the subject compositions is deemed to include the free form composition, solvent adducts, and chelates of said composition.

A process for preparing the invention compositions is also a subject of this invention and comprises contacting a solution of a metal complex of the formula: $L_aL_b'L_c''MH_mX_n$, or adduct thereof, wherein $L_a$, $L_b'$, $L_c''$, as are defined hereinabove for the subject compositions, H being hydrido, X being halide, m being an integer value of from 0 to 3 and n being an integer value of from 0 to 3, in an inert solvent therefor, with a solution of Group IA metal arene, $T^+Ar^-$, wherein T is a Group IA metal, and Ar is an aromatic moiety, containing 6 to 14 carbon atoms, in an inert solvent therefor, under a dry inert atmosphere, at a temperature from about $-111°$ C. to $+80°$ C., wherein the Group IA metal arene is present in an initial amount of at least about $n+1$ equivalents per equivalent of halide in the metal complex desired to be replaced, n being defined as above. Thus, at least one equivalent of metal arene should be used in excess over the equivalents of halide present in the metal complex, and preferably, no more than about 10 percent equivalent excess over the one equivalent in excess.

The resulting subject composition containing a cation, being a Group IA metal, can be contacted with a salt, soluble in the solvent used for the resulting composition, wherein the salt contains a cation Q being other than a Group IA metal, as defined for the subject composition hereinabove. The contacting results in a "cationic exchange" between the dissolved salt and initial resulting subject composition resulting in the subject composition now containing cation Q being other than a Group IA metal as defined above.

Metal complexes, applicable in the process for producing the invention compositions, contain a Group VIII metal atom, 1 to 3 organoligands per Group VIII metal atom, as described hereinabove. Further, the metal complexes can contain 0 to 3 hydrogen atoms, and 0 to 3 halide atoms, being fluoride, chloride, bromide and iodide and preferably chloride. Thus, the term metal complex includes Group VIII metal halides, hydridohalides, hydrides and neutral metal complexes containing organoligands as described herein. The metal complex can be in the free form, or can be in adduct form with a solvent, such as diethylether, tetrahydrofuran, toluene and the like. Representative examples of metal complexes applicable in the invention include $(Ph_3P)_3RuHCl$, $[(Ph_3P)_2RuHCl]_2$, $[(Ph_3P)_2RhHCl]_2$, $(Ph_3P)_2FeBr_2$, $(Ph_3P)_2PtHCl$, $(Ph_3P)_3RhH_2Cl$, $(Ph_3P)_3IrH_2Cl$, $(Ph_3P)_2RuCl_3$, $(Ph_3P)_2IrH_3$, $(Ph_3P)_3CoH_3$, $(Ph_3P)_3RhCl$, $(Ph_3P)_3Pt$, $(Ph_3P)_3RhH$, $(Ph_3P)_3RuH_2$, $[Ph_2PCH_2CH_2PPh_2RhCl]_2$ and $[(Ph_3P)_2RhCl]_2$.

The Group IA metal arene, $T^+Ar^-$, useful in the invention process contains the metal cations of lithium, sodium, potassium, rubidium and cesium. Preferred cation in the process is potassium. Once having formed the subject composition containing a Group IA metal cation, the Group IA cation can be replaced during an exchange reaction with the cation of an added soluble salt. This is necessary in cases where the cation is incapable of forming a metal arene in the reaction process and is applicable to cations Q, being other than a Group IA metal as defined hereinabove. The added salt is preferably chosen such that the salt formed between the anion of the added salt and the cation Q to be replaced, forms an insoluble salt under the circumstances. For example, the potassium salt of a subject composition anionic hydride radical can be replaced by reaction with magnesium bromide in tetrahydrofuran. Formed potassium bromide is much less soluble in diethyl ether and is easily separated from the resulting magnesium salt of the anionic hydride. Examples of other salts that can be used in the process include lanthanum bromide, aluminum chloride, $(C_5H_5)TiCl_3$ and $[(C_5H_5)_2TiCl]_2$. Representative examples of subject compositions containing cations, Q, which can't be directly prepared in the subject process but must be prepared by exchange reaction are $La^{+3}$, $Mg^{+2}$, $Al^{+3}$ and $(C_5H_5)_2Ti(III)^+$ cation salts of the subject compositions.

The "arene", is an aromatic radical anion, formed from an aromatic compound containing 6 to 14 carbon atoms and is formed from benzene, toluene, naphthalene, biphenyl, anthracene, phenanthrene, and the like. Preferred aromatic compound as the arene is naphthalene anion. Representative examples of metal arenes include lithium naphthalene, sodium naphthalene, potassium naphthalene, cesium naphthalene and potassium biphenyl. Preferred metal arene is potassium naphthalene.

Solvents applicable in the process must be polar and include $C_4$–$C_6$ cyclic saturated aliphatic mono- or diethers, $C_2$–$C_6$ cyclic saturated aliphatic mono- or diethers, $C_7$–$C_{14}$ aromatic ethers, and $C_3$–$C_8$ saturated aliphatic tertiary mono- and diamines. Representative examples of solvents include tetrahydrofuran, anisole, diphenylether, diglyme, dioxane, diethyl ether, 1,2-dimethoxyethane, trimethylamine, triethylamine, and N,N,N',N'-tetramethylethylenediamine. Preferred solvent is tetrahydrofuran.

Amount of solvent used in the process is generally about 10–100 parts by weight per part of metal complex. The amount of solvent is not critical and smaller or larger amounts may be used with the proviso that sufficient solvent is present to dissolve the metal complex and metal arene to initiate and maintain the reaction.

The process can be conducted at a temperature from about $-111°$ L C. to $+80°$ C. Temperatures below $-80°$ C. will lead to highly pure compositions in the process, but a temperature in the range from 0° to 30° C. is preferred since it is more convenient and produces the invention compositions in acceptable purity for use in hydrogenation processes.

The process can be conducted under any convenient pressure, e.g. at reduced pressure, such as that of the solvent vapor, or using an inert gas at atmospheric pressure, or above, such gas being in particular, dry nitrogen or argon, and preferably argon. It is preferred, from the standpoint of convenience and economy, to carry out the process at atmospheric pressure under a dry inert atmosphere, preferably consisting essentially of argon or nitrogen.

The amount of metal arene used is generally about $n+1$ equivalents per equivalent of halide in the metal complex desired to be replaced. Where no halide is present in the metal complex, one equivalent of metal arene is employed, per metal atom. Preferably, the stoichiometric ratio of n+1 equivalents metal arene/equivalent of halide is used. However, no more than about a 10 percent equivalent excess should be used over the stoichiometric quantity.

Apparatus which is used to carry out the process can be of any conventional type in which the steps of addition of reagents, heating, cooling, isolation and purification procedures can be carried out under an inert dry atmosphere and include the use of conventional dry boxes, glove-bags and conventional vacuum equipment. Apparatus which is useful is an H-shaped hollow glass evacuable cell in which the horizontal portion serves as a filtering device and the vertical sides of the "H" serve as the reaction vessel. Description of the above apparatus, and a more convenient apparatus for larger scale reactions plus a method of making and using is described in *J. Amer. Chem. Soc.*, 98, 8072 (1976), hereby incorporated by reference.

A preferred embodiment of the process is where the solvent is tetrahydrofuran, the temperature is $-80°$ C., the pressure is less than $10^{-3}$ atmospheres, and the atmosphere consists essentially of solvent vapor. Argon or nitrogen can also be used as inert gases over the reaction mixture during the process.

Yields of anionic hydride compositions from the process are in the range of about 50 to 90 percent of theory based on starting metal complex including the process when utilizing the cationic exchange reaction.

In addition there is provided a second invention process, for producing the subject composition, directed to the step of contacting a solution comprised of a metal complex of the formula: $L_aL_b'L_c''MH_mX_n$, or adduct thereof, wherein $L_a$, $L_b'$, $L_c''$ and M are defined as hereinabove, H being hydrido, X being halide, m being an interger value of from 0 to 3 and n being an integer value of from 0 to 3, in an inert solvent therefor, with a suspension of Group IA metal hydride in an inert solvent therefor, under a dry inert atmosphere, at a temperature from about $-20°$ C. to $+150°$ C., wherein the Group IA metal hydride is present in an initial amount of about n+1 equivalents per equivalent of halide in the metal complex desired to be replaced, n being defined as above, thereby resulting in the subject composition wherein cation Q is a Group IA metal.

The elements of this second process, with respect to the amounts and nature thereof of metal complex, inert solvent, inert atmosphere, equivalents of reagent used, pressure, apparatus and yields, are equivalent to and equally described in the first abovedescribed process and need not be reiterated.

The second process is similar to the first process and differs therein that a Group IA alkali metal hydride, being a hydride ion donor, is used instead of a metal arene, being an electron donor. The action of both reagents on the above-described metal complex results thereby in the subject composition as defined by the given formula. It should be noted that even though both processes give compounds fitting the general formula, the processes yield different product species of the genus composition when greater than n+1 equivalents of metal hydride or metal arene are reacted with n equivalents of the same starting metal complex. See Examples 2 and 9.

Since the alkali metal hydride is only very slightly soluble in the applicable solvents, the reaction is essentially heterogeneous and the optimum temperature range is from about $-20°$ to $+150°$ C. as compared to the first described process and preferably in the range of $20°-80°$ C.

Another difference is that use of an excess of alkali metal hydride, above n+1 equivalents, will occasionally result in an unexpected product. For example, contacting $[(Ph_3P)_2RuHCl]_2$ with an excess of potassium hydride, above n+1 equivalents, results in the product, $[(Ph_3P)_3RuH_3]_2^-K^+$, rather than $[(Ph_3P)_2RuH_3]^-K^+$. Accordingly, a preferred embodiment of the second invention process is wherein $[(Ph_3P)_2RuHCl]_2$ is contacted with an excess of potassium hydride, above n+1 equivalents, up to 20 equivalents based on the value of n, under the above-described process conditions.

The subject compositions described herein are useful as catalysts in the homogeneous hydrogenation of aldehydes, ketones, olefins and alkynes.

Thus, also subjects of this invention are improved processes for hydrogenating an aldehyde group to a primary alcohol group, a ketone group to a secondary alcohol group, an ethylenic bond to a saturated aliphatic bond, and an acetylenic bond to an ethylenic bond or saturated aliphatic bond, or mixtures thereof, in a chemical compound, respectively, including contacting a solution of hydrogenation catayst and the respective compound, neat or in an inert solvent therefor, with an atmosphere containing hydrogen gas; the improvement which comprises providing the subject compositions described herein as said hydrogenation catalyst.

Prior art processes for catalytically hydrogenating aldehydes, ketones, olefins and alkynes under homogeneous conditions are known in the art and are respectively described in J.C.S. Chem. Comm. 923 (1967); J.C.S. Chem. Comm. 567 (1970) and J. Chem. Soc. (A) 1711 (1966); in which the respective conditions for hydrogenation, are hereby incorporated by reference. Generally the processes can be conducted at a temperature of about $0°$ to $250°$ C. and at a pressure of about 0.1 to 500 atmospheres.

Details regarding the process with respect to typical solvents used, process conducted under neat conditions, catalyst concentration, substrate concentration, reaction temperature range, pressure, methods of isolation and purification, yields and selectivities of products in the processes are all described in the prior art and need not be reiterated herein.

The novelty of these improved processes is the discovery that the subject compositions are surprisingly effective catalysts for the respective catalytic homogeneous hydrogenations.

Preferred subject compositions for reduction of aldehydes, ketones, olefins, and alkynes are subject compositions corresponding to Roman Numerals I and II, described hereinabove.

Representative aldehydes applicable in the improved process, being hydrogenated to the corresponding primary alcohol are: acetaldehyde, propanal, acrolein, and the like.

Representative ketones applicable in the improved process, being hydrogenated to the corresponding secondary alcohol are: acetone, methylethyl ketone, hexafluoroacetone, cyclohexanone, benzophenone, and the like.

Representative olefins applicable in the improved process, in which the ethylenic bond is hydrogenated to the corresponding saturated aliphatic bond are: acrolein, 1-hexene, 2-hexene, cyclohexene, and the like.

Representative alkynes applicable in the improved process, in which the acetylenic bond is hydrogenated to the corresponding ethylenic bond or saturated aliphatic bond, or mixtures thereof, are 2-hexyne, 1-hexyne and the like.

The following examples are illustrative of the best mode of carrying out the invention as contemplated by us and should not be construed to be limitations on the spirit or scope of the instant invention.

GENERAL

All the anionic hydride compositions are extremely air sensitive and were prepared and handled by a combination of high vacuum line and argon dry-box techniques. Solvents of chromatoquality were further purified by treatment with $LiAlH_4$, potassium anthracene (ethers), or with Na/K alloy (aromatics, alkanes). Polar solvents (acetone) were simply dried with molecular sieves. Ultrahigh purity $N_2$, Ar and $H_2$ gases were used.

EXAMPLE 1

Preparation of potassium tris(triphenylphosphine) ruthenium hydride

This synthesis depends on the reduction of tris(triphenylphosphine)ruthenium hydridochloride with two moles of potassium naphthalene according to the equation:

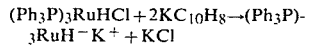
$(Ph_3P)_3RuHCl + 2KC_{10}H_8 \rightarrow (Ph_3P)_3RuH^-K^+ + KCl$

For this synthesis a special apparatus was used, equipped for stirring solutions at low temperature as described in *J. Amer. Chem. Soc.*, 98 8077 (1976). The upper bulb of the apparatus (500 ml capacity) was charged, under an argon atmosphere, with 0.4 g of potassium metal (10.2 mmoles), and 1.4 g of naphthalene (10.9 moles). The lower bulb was charged with 5 g of tris(triphenylphosphine)-ruthenium hydridochloride, $(Ph_3P)_3RuHCl$-toluene, (95.41 mmoles). [The latter was prepared from tris(triphenylphosphine)ruthenium dichloride, following the procedure described in *J. Chem. Soc. (A)* 3143 (1968). Tetrahydrofuran was distilled into the two bulbs (ca 150 ml). The mixture in the upper bulb was stirred at room temperature until dissolution of potassium (to yield green potassium naphthalene) was complete. Both flasks were then cooled to −80° C. The cold potassium naphthalene solution was then added slowly to the well-stirred slurry of the ruthenium hydridochloride complex at −80° C. (or at −111° C.). The resulting reddishyellow solution was stirred at −80° C. (16 hours), −35° C. (5 hours), −16° C. (5 hours) and then warmed to room temperature. It was evaporated to near dryness and n-octane (50 ml) added. After some agitation and vacuum pumping, a dry yellowgreen solid remained. This was extracted repeatedly with diethyl ether, giving a filtrate which, when dried and washed with ether, afforded 3.4 g of a bright yellow solid, which we regard as being impure $(Ph_3P)_2(Ph_2PC_6H_4)RuH_2^-K^+.(Et_2O).C_{10}H_8.$ (A similar material of only slightly lower purity, was obtained by conducting the above-described process at 0°-25° C., under an atmosphere of very pure nitrogen gas at a pressure of one atmosphere).

This material was purified by double crystallization from diethyl ether solutions containing excess naphthalene. The crude material (3 g) and $C_{10}H_8$ (7.7 g) and 390 ml $(C_2H_5)_2O$ were loaded into an H-shaped apparatus, with the two vertical arms separated by a filter frit. The amber ether solution was filtered and the apparatus left in a cold room at 3°-4° C. After it had equilibrated at this temperature, the other leg of the H-tube was put in a Dewar container of ice water (0° C.). Slow evaporation to near (but not total) dryness afforded a mass of yellow crystals. These were washed with diethylether and redissolved to yield a bright yellow orange solution. Slow evaporation, as before, gave yellow crystals and a green supernatant solution. Yield of the ether washed crystals (collected without evacuation, under an atmosphere of argon) was 2.2 g. Elemental Analyses (by a commercial laboratory): Found (mean of duplicate analyses): C, 71.53; H, 5.74; P, 8.41; K, 3.68. Calculated, on the basis of formula $[(Ph_3P)_3RuH]^-K^+.(C_2H_5)O.C_{10}H_8$: C, 72.31; H, 5.62; P, 8.22; K, 3.46. The presence of the triphenylphosphine, diethylether and naphthalene was established by proton NMR. Reaction of the above-prepared compound with HCl and $CH_3I$ gave two moles of hydrogen and two moles methane, respectively, per mole of compound, implying that there are two hydride atoms per ruthenium atom in the compound.

Two infrared absorption bands for the metal-hydride bonds were observed in the region of 1735 and 1825 $cm^{-1}$. Metal hydride signals were also observed in the proton NMR spectrum at $(CH_3)_4Si$, −7.0 and −11.0 ppm.

EXAMPLE 2

Preparation of potassium triphenylphosphine-diphenyl phosphide ruthenium hydride (A) Synthesis of bis(triphenylphosphine)ruthenium trichloride methanol This method is a modification of the procedure described in *J. Inorg. Nucl. Chem.* 28, 945 (1966). Ruthenium trichloride hydrate, was dissolved in 2400 ml of reagent methanol. Lithium chloride (150 g) was added slowly over 30–40 minutes. Triphenylphosphine (24 g, finely powdered) was sprinkled slowly (over 30 minutes) into the rapidly stirred solution. This was filtered, and the filtrate was equally divided and placed into four 1-liter flasks and put on a shaker. After three days, a total of 4.2 g of a green precipitate, was collected. A further 20 g of $PPh_3$ was then added which, after a week of shaking at room temperature, offered an additional 12 g of the green product. A third charge of of $PPh_3$ was added. Total yield of $(Ph_3P)_2RuCl_3.CH_3OH$, with this preparation, ranged from 25–35 g. Analysis of product; Found: P, 7.12%, Cl, 11.59%. Expected: P, 8.11%; Cl, 13.9%.

(B) Preparation of bis (triphenylphosphine) ruthenium hydridochloride, dimer

Proceeding by a modification of the method described in *J. Chem. Soc. Chem. Comm.* 792 (1976), to 19.4 g of $(Ph_3P)_2RuCl_3.CH_3OH$ (green) in a 50 ml dumbbell-shaped apparatus (with the two bulbs separated by a filter frit) was added toluene and 14 ml of dry triethylamine. To the stirred mixture (while still cold) was added $H_2$ gas (1 atm). The color changed from green to reddish-brown after 10 minutes stirring at room temperature. The reaction took up $H_2$ for 20 hours, and afforded a reddish solution. The toluene and other volatiles were removed, and the dark brown mass washed with 30 ml fresh toluene and dried. It was then extracted repeatedly with dry, degassed ethanol until no traces of $Et_3N \cdot HCl$ remained. Yield was 10 g of a reddish powder. Analyses: Found: C, 66.88; H, 5.20; P, 8.65; Ru, 12.27; Cl, 4.76. Calculated for $(Ph_3P)_2RuHCl \cdot C_6H_5CH_3$: C, 68.48; H, 5.21; P, 8.21; Ru, 13.40; Cl, 4.70. The solid exhibited a weak to medium infrared absorption maximum at 2040 cm$^{-1}$; characteristic of a terminal metal hydride.

(C) Reduction of $[(Ph_3P)_2RuHCl]_2$ toluene adduct

For this synthesis, the same apparatus and procedure were employed as described in Example 1. The apparatus was charged under an argon atmosphere with 0.90 g of potassium metal (23.0 mmoles) and 3.35 g naphthalene (26.2 mmoles) (upper bulb) and with 8.5 g bis(triphenylphosphine)ruthenium hydridochloride.toluene dimer (11.4 mmoles based on Cl analysis) (lower bulb). Tetrahydrofuran (150 ml) was added to each bulb. A solution of potassium naphthalene at −40° C. to −80° C. was slowly added to the hydridochloride at −111° C. The mixture was stirred at −80° C. (1 day), −35° C. (5 hours), −16° C. (5 hours) and then warmed to room temperature and filtered. The filtrate was evaporated to a small oily residue and dried by treatment with octane. A redbrown solid product (7.5 g) remained. Extraction of this crude product with diethyl ether afforded two materials: (a) an ether soluble brown substance which we believe to be of the structure: $(PPh_3)_2Ru^-H^+$(1.4 g) and (b) an ether-insoluble reddish solid which we believe to be structure (II), $[(Ph_3P)(Ph_2P)RuH] K$ (1.1 g.). Elemental analysis of the ether-soluble extract: (by a commercial laboratory): Found: C, 64.11; H, 4.92; P, 9.33; K, 4.85. Calculated for $[(Ph_3P)_2RuH]^-K^+$: C, 64.95; H, 4.69; P, 9.30; K, 5.87. The ether-insoluble compound was purified by placing 600 mg of the material in an H-shaped tube and then toluene (60 ml) and diglyme (2.5 ml) were added. A layer of 180 ml of isopentane was placed over this solution and left to diffuse slowly over 6 weeks at 4° C. Dark needle crystals (120–180 mg) and some reddish precipitate were obtained. Analyses of crystals (which contain diglyme as seen in the proton nuclear magnetic resonance spectrum); Found: C, 59.88; H, 5.51; P, 8.23; K, 6.05. For $[(Ph_3P)(Ph_2P)RuH]^-K^+ \cdot (CH_3OCH_2CH_2)_2O$, the calculated elemental percentages are C, 59.90; H, 5.45; P, 8.23; K, 5.41. On the basis of these elemental analyses, the proton, and P$^{31}$ nuclear magnetic spectra, and results of reaction of the composition with HCl and CH$_3$I, we believe the structure of the composition to be the dimeric form:

$$[(Ph_3P)(Ph_2P)RuH_2]_2^- K_2^+ [(CH_3OCH_2CH_2)_2O]_2$$

EXAMPLE 3

Preparation of potassium tris(triphenylphosphine) rhodium hydride

This preparation depends on the reduction of tris(triphenylphosphine)rhodium hydride with potassium naphthalene according to the equation:

$$(Ph_3P)_3RhH + KC_{10}H_8 \rightarrow (Ph_3P)_3RhH^-K^+$$

The $(PPh_3)_3Rh$-H starting material was made by a very convenient technique developed by S. Diamond and F. Mares (J. Organomet. Chem., 142, C55, 1977). It involves reaction of $(Ph_3P)_3RhCl$ with lithium dimethylamide in tetrahydrofuran to yield, $(Ph_3P)_3Rh$—H. This product was purified by recrystallization from tetrahydrofuran.

The reduction of the above-prepared hydride with potassium naphthalene, was carried out as follows:

An H-shaped apparatus, described above, with the vertical arms separated by a horizontal filter tube, was loaded on one side with 1.2 g $(Ph_3P)_3RhH$ (1.25 mmole) and on the other side, with 49 mg of potassium metal (1.25 mmoles) and 190 mg naphthalene (1.5 mmoles). Very pure tetrahydrofuran (20 ml) was distilled into each side of the H-tube, and the $K/C_{10}H_8$ mixture stirred until dissolution of the K metal to yield green potassium naphthalene was complete. The reddish solution of $(Ph_3P)_3$ RhH was cooled to −111° C. and the solution of $K^+C_{10}H_8$ in THF, was added to it dropwise, with stirring over about 2 hours. When the addition was complete, the solution was stirred at −111° C. for 1 hour, then at −80° C. for 8 hours, and then slowly allowed to warm to room temperature. There resulted a deep brown solution, which was evaporated to total dryness. This residue was extracted with tetrahydrofuran to yield a brown, air-sensitive powder (600 mg). Analyses for all the elements (including K) was in rough agreement with the structural formula: $(Ph_3P)_3RhH^-K^+$. However, the exact structure of the molecule may be more complex.

One mole of the crude solid reaction product reacted with excess hydrogen chloride and produced about ⅔ mole of hydrogen gas.

EXAMPLE 4

Preparation of dipotassium bis(diphenylphosphido) iron hydride

This preparation involves reducing bistriphenylphosphine iron dibromide $(Ph_3P)_2FeBr_2$(one mole) with (three moles) of potassium naphthalene at low temperatures.

The bistriphenylphosphine iron dibromide starting material was prepared by a modification of the method described in J. Chem. Soc. 2099 (1962), using FeBr$_2$ instead of FeCl$_2$.

An H-shaped apparatus, described above, was used as in the previous example. One side of the H-shaped apparatus was charged with 5 g $(Ph_3P)_2FeBr_2$; the other side with 0.845 g potassium and 3.1 g of naphthalene. Tetrahydrofuran was added, and the solution stirred until formation of potassium naphthalene was complete. The green potassium naphthalene solution was then added slowly to the solution of $(Ph_3P)_2FeBr_2$, cooled to −111° C. It was stirred at −111° C. for 2 hours, at −80° C. for 16 hours, and then slowly allowed to warm to room temperature. The resultant brown solution was evaporated to dryness in vacuum and the residue washed with ether to yield a black solid product (1.8 g). On the basis of the elemental analyses and chemical reactivity data (measurement of H$_2$ evolution upon treatment with acid) we regard the resulting composition to be of the formula:

$$[(Ph_2P)_2Fe_2H]^= K_2^+.$$

EXAMPLE 5

Preparation of lithium tris(triphenylphosphine)ruthenium hydride

The procedure used was similar to that described in Example 1, except that the equivalent amount of lithium naphthalene was used instead of potassium naphthalene. The lithium naphthalene was prepared by dissolving lithium powder (about 500 mesh) or Li ribbon, in tetrahydrofuran, analogous to the preparation of potassium naphthalene.

Reduction of $(Ph_3P)_3RuHCl$·toluene (5 g) with Li (0.76 g) and $C_{10}H_8$ (1.6 g) (as lithium naphthalene) at $-80°$ C., followed by slow warming to room temperature, and extraction of the product with diethylether (as in Example 1), afforded a light yellow solid (3.7 g). The infrared spectrum of the product gave a single, broad, intense infrared band at 1810 cm$^{-1}$, in contrast to the 1735, 1825 cm$^{-1}$ doublet observed for the potassium compound. The infrared spectrum showed the presence of naphthalene. Elemental analyses of this material was in accordance with the structural formula: $(Ph_3P)_3RuH^-Li^+(Et_2O)\cdot C_{10}H_8$. The product resisted attempts at purification by recrystallization, and thus was not characterized exhaustively. However, by analogy with the K$^+$ compound we regard the compound likely to be dihydride having one ortho-metallated triphenylphosphine ligand, and two triphenylphosphine ligands coordinated to ruthenium.

EXAMPLE 6

Preparation of magnesium bis[tris(triphenylphosphine)ruthenium hydride]

Alkaline earth and other metals that do not form radical anion solutions with polynuclear aromatics, can be coupled with the anionic ruthenium complex hydrides by a cationic exchange technique. For the preparation of the magnesium derivative of $[(Ph_3P)_3RuH]^-K^+$, a solution of $MgBr_2$ (24 mg) in diethyl ether (20 ml was slowly added to a solution of 220 mg of $[(Ph_3P)_3RuH]^-K^+$·toluene, also in diethyl ether. Upon addition of the $MgBr_2$ the bright yellow solution darkened to a beige color. The mixture was stirred for 8 hrs., at $-80°$ C., under an inert atmosphere of solvent vapor, then slowly warmed to room temperature with stirring. A light brown solid having a metal hydride stretching frequency at about 1760 cm$^{-1}$, was recovered.

EXAMPLE 7

Preparation of lithium and cesium bis(triphenylphosphine) ruthenium hydrides

These compositions were prepared by reduction of bis(triphenylphosphine) ruthenium hydridochloride with lithium and cesium naphthalene, respectively, using the same methods as described in Example 6.

Following the procedure described in Example 6, reduction of $(Ph_3P)_2RuHCl$·toluene dimer with lithium naphthalene, afforded a red-brown solid. This was purified by extraction with toluene. The infrared spectrum of the product showed a weak to medium intensity metal-hydride band at 1800 cm$^{-1}$. Elemental analyses were consistent with the formulas: $[(Ph_3P)_2RuH]^-Li^+$ or $[(Ph_3P)(Ph_2P)RuH]^-Li^+$.

The cesium analog was prepared by reduction of $(Ph_3P)_2RuHCl$·toluene dimer with cesium naphthalene. The latter was prepared by mixing cesium metal with a solution of naphthalene in tetrahydrofuran, at $-80°$ C., then slowly warming to room temperature until all the cesium metal had dissolved. Reaction of $CsC_{10}H_8$ (from 1.1 g of Cs and 1.2 g $C_{10}H_8$) with the $(Ph_3P)_2RuHCl$·toluene dimer, as described in Example 6, afforded a brown powder. The latter was washed with diethyl ether to yield an ether insoluble red-brown product, the latter having a metal-hydride stretching frequency at 1800 cm$^{-1}$.

EXAMPLE 8

Preparation of potassium tris(methyldiphenylphosphine) ruthenium hydride

This is a three-part synthesis, starting from ruthenium trichloride and methyldiphenylphosphine.

(A) Preparation of lithium bis(methyldiphenylphosphine) ruthenium tetrachloride methanol.

A 100 ml Schlenk round bottom flask was charged with 500 ml of degassed methanol. To this solution, lithium chloride (75 g) was added slowly over a 30 minute period. After the solution had cooled to room temperature, $RuCl_3\cdot 3H_2O$ (3 g, 11.5 mol), was added and then methyldiphenyl phosphine (6 g, 30.0 mmol) was added quickly via a syringe. The reaction mixture was filtered immediately under nitrogen to separate a grey-black precipitate from the green solution. The reaction mixture was allowed to stir at room temperature for three days and filtered under nitrogen. The green precipitate was washed with three portions of 50 ml of degassed methanol, followed by one 50 ml portion of degassed diethyl ether. The green precipitate was dried, in vacuo, resulting in a 50% yield of $(Ph_2CH_3P)_2 RuCl_4Li\cdot CH_3OH$ (4 g, 5.75 mmol). Analysis for $C_{27}H_{30}P_2 Cl_4LiRuO$: Calculated; C, 47.53; H, 4.43; P, 9.08; Cl, 20.78. Found: C, 46.69; H, 4.26; P, 8.50; Cl, 20.10; Li, was qualitatively detected. The presence of methanol in the compound was also supported by the presence of a strong broad band at 3340 cm$^{-1}$ in the infrared absorption spectrum (Nujol).

(B) Preparation of bis[bis(methyldiphenylphosphine) ruthenium chloride] hydride.

An H-shaped tube equipped with a filter disc in the horizontal portion was charged with $(Ph_2CH_3P)_2 RuCl_4Li\cdot CH_3OH$ (2 g, 2.87 mmol) and 60 ml of tetrahydrofuran (THF) followed by triethylamine (1.4 g, 14.3 mmol), distilled onto the solid in vacuo. The green reaction mixture was then pressurized with 780 mm of hydrogen and allowed to react at room temperature for three days. The green reaction mixture became a homogeneous dark brown solution. The THF was removed in vacuo and 60 ml of toluene was distilled in. The solution was filtered and the toluene removed in vacuo leaving a brown-black residue. The residue was stirred with 30 ml. of petroleum ether (30°-60° C.) and filtered. Drying the precipitate in vacuo gave a 63% yield of a compound characterized as: $[(Ph_2CH_3P)_2RuCl]_2H$ (1.0 g, 1.75 mmol). Analyses for $C_{26}H_{27}P_2RuCl$: Calculated: C, 58.05; H, 5.06; P, 11.51; Cl, 6.59. Found: C, 57.75; H, 5.51; P, 11.57; Cl, 6.24. The presence of a metal-hydride bond is indicated by the presence of a weak broad absorption at 1975 cm$^{-1}$ in the IR (Nujol) and the liberation of approximately 1 mol of $H_2$/per mole of $[(Ph_2CH_3P)_2RuCl]_2H$.

(C) Reduction of $[(Ph_2CH_3P)_2RuCl]_2H$ with potassium naphthalene.

A solution of potassium naphthalene was prepared from potassium (110 mg) and naphthalene (400 mg), in tetrahydrofuran (40 ml). This was added to a suspension of $[(Ph_2CH_3P)_2RuCl]_2H$ (780 mg) in 40 ml of tetrahydrofuran, cooled to $-111°$ C. The reducing metal arene solution was added slowly, and the reaction mixture, at $-111°$ C. was vigorously agitated throughout the addition. The solution was then warmed to $-80°$ C., and stirred for 18 hours at this temperature, then slowly warmed to room temperature. The resultant solution was filtered and evaporated to dryness giving a dark brown solid. The latter gave a broad metal-hydride absorption band in the infrared region at 1800 cm$^{-1}$. On the basis of the elemental analyses of this crude product, we regard the composition as being [(Ph$_2$CH$_3$P)$_3$RuH]$^-$K$^+$.

EXAMPLE 9

Synthesis of bis[tris(triphenylphosphine)ruthenium tris(hydrido)]potassium: [(Ph$_3$P)$_3$RuH$_3$]$_2$$^-$K$^+$ The title composition was prepared by reaction of [bis(triphenylphosphine)ruthenium hydridochloride]-toluene with excess potassium hydride in tetrahydrofuran, according to the following formula:
[(Ph$_3$P)$_2$RuHCl]$_2$·toluene$_2$ + excess KH $\xrightarrow{THF}$ [(Ph$_3$P)$_3$RuH$_3$]$^-$K$^+$ To the apparatus described in Example 3, under an argon atmosphere, was charged [(Ph$_3$P)$_2$RuHCl]$_2$·toluene$_2$ (5.0 g) and finely powdered, dry potassium hydride (2.5 g). Tetrahydrofuran (140 mL) was distilled into the apparatus, and the resulting slurry was stirred for 5 days at 20°–25° C. During this time the ruthenium hydridochloride complex (which is only partially soluble in tetrahydrofuran) was dissolved by reaction with KH to yield a deep brown solution. This was evaporated in vacuum at room temperature, and dried to a brown powder by successive washings with n-octane. The powder was then extracted repeatedly with diethyl ether. Evaporation of the ether extracts afforded a dark solid. This was extracted with hexane, leaving a reddish-colored residue which was dried under vacuum. Yield of this crude product was 2.4 g. Samples of this material were purified by crystallization from diethyl ether solutions of the crude product in the above described apparatus. A diethyl ether solution was filtered, and was very slowly evaporated to near dryness by maintaining a 1°–2° C. temperature difference between the two vertical legs of the apparatus. A reddish, fine crystalline product was formed on the sides of the tube. It was washed with a little diethyl ether and finally collected and stored under an argon atmosphere.

The crystalline product was characterized by a combination of chemical and spectroscopic techniques. Elemental analyses showed that the approximate atomic ratios for K:P:Ru was 1:6:2. Elemental analyses; Found: K, 1.9; P, 9.1; C, 67.5; H, 5.7; Ru, 10.4. Calculated: K, 2.15; P, 10.21; C, 71.23; H, 5.27, Ru, 11.10. The number of hydridic hydrogen atoms was determined by measuring the amount of H$_2$ evolved upon treatment of the complex with hydrogen chloride in tetrahydrofuran. Found: 5.3 moles H$_2$/mole of complex. A more precise measure of the number of metal hydride atoms was obtained from $^{31}$P-decoupled $^1$H NMR spectra, which at 270 MHz showed six signals to high field of tetramethylsilane:

$\delta$(CH$_3$)$_4$Si −8.60, −9.13, −10.15, −16.52, −19.72 and −20.62. (Transition metal hydrides typically give $^1$H NMR signals at high field strengths with respect to tetramethylsilane, ([CH$_3$]$_4$Si).) A further characteristic of the complex is the presence of metal hydride absorptions in the infrared. Infrared spectra of the compound suspended in Nujol displayed a complex set of intense absorption bands in the region from 1800–2000 cm$^{-1}$ with maxima occurring at 1850, 1900 and 1940 cm$^{-1}$. Other bands in the infrared are typical of those seen for triphenylphosphine metal complexes. On the basis of the above data, we believe that the compound formed is potassium bis[tris(triphenylphosphine)ruthenium trihydride] [(Ph$_3$P)$_3$RuH$_3$]$^-$$_2$K$^+$.

EXAMPLE 10

Preparation of potassium bis[bis(triphenylphosphine) rhodium] monohydride, [(PPh$_3$)$_2$Rh]$_2$H$^-$K$^+$ Bis[bis(triphenylphosphine) rhodium chloride] (3.0 g) (prepared according to the reference: *J. Chem. Soc.* (A), 1711 (1966) and potassium hydride powder (1.5 g) were charged under an inert atmosphere into one leg of the apparatus described in Example 1. Tetrahydrofuran (30 mL) was distilled in over the mixture. An evacuated bulb of 250 cc capacity was attached to the apparatus (to contain any H$_2$-gas that might be evolved during the preparation). Argon gas (50 cc) was added to the system, and the [(PPh$_3$)$_2$RhCl]$_2$/KH/-tetrahydrofuran mixture was heated to 62° C. and stirred rapidly for 18 hours. During this time, the orange mixture is tetrahydrofuran changed to a deep brown solution. This was evaporated to dryness in vacuum and the resulting solid was extracted with diethyl ether. Evaporation of the diethyl ether extracts yielded a dark brown powder (1.4 g). On the basis of the elemental analyses and chemical reactivity of the latter product, we believe its formula to be: [(PPh$_3$)$_2$Rh]$_2$H$^-$K$^+$. Elemental 2 analyses: Found: C, 63.83; H, 5.60; P, 9.90, Rh, 15.73; K, 3.28; Cl, trace (0.5%). Theory: C, 66.77; H, 4.75; P, 9.57; Rh, 15.89; K, 3.01. Reaction of the compound (52.25 mg) with methyl iodide gave product methane in an amount which corresponds to 0.96 mol of hydridic hydrogen per mol of compound.

EXAMPLE 11

Hydrogenation of Acetone

A. A glass pressure tube was charged with 40 mg of the bright yellow tris-phosphine composition obtained in Example 1, [(Ph$_3$P)$_2$(Ph$_2$PC$_6$H$_4$)RuH$_2$]$^-$K$^+$, and 4 grams (69 mmol) of acetone. The reaction solution was pressurized to 100 psi of hydrogen and allowed to react at 80° C. for 16 hours. The reaction mixture was repressurized to 100 psi three times during this time period, each time the hydrogen pressure reached 40 psi. Gas chromatographic analysis of the reaction mixture showed 92% conversion of acetone to products. The resulting product mixture consisted of 90% by weight isopropanol, 5% by weight 4-methyl-2-pentanone, 3% by weight 4-methyl-2-pentanol and 2% by weight various other higher boiling products.

B. A glass pressure tube was charged with 40 mg. of the very pure crystalline trisphosphine catalyst, [(Ph$_3$P)$_2$(Ph$_2$PC$_6$H$_4$)RuH$_2$]$^-$K$^+$·C$_{10}$H$_8$·(C$_2$H$_5$)$_2$O, obtained in Example 1, 3 ml of toluene and 0.79 gram (13.6 mmol) of acetone. The reaction mixture was allowed to react at 85° C. for 16 hours. Gas chromatographic analysis of the reaction mixture showed a 95% conversion of acetone to isopropanol in high selectivity (98%) and no additional products were detected. Thus, higher conversions and selectivities are obtainable from very pure catalyst in this case as opposed to the crude catalyst obtained directly from Example 1, used in part A above.

C. A glass pressure tube was charged with 20 mg of the bis-phosphine catalyst [(Ph$_3$P)(Ph$_2$P)RuH$^-$K$^+$]$_2$, 3 mL of toluene and 1 ml of acetone. The reaction solution was pressurized to 90 psig of hydrogen and allowed to react at 85° C. for 4 hours. Analysis of the reaction mixture by gas chromatography showed 100% conversion of the acetone to isopropanol with 97% selectivity.

D. A glass pressure tube was charged with 20 mg of $[(Ph_3P)_3RuH_3]^-{}_2K^+$ 3 ml of toluene and 0.5 ml of acetone The reaction solution was pressurized to 90 psig of hydrogen and allowed to react at 85° C. for five hours. Analysis of the reaction mixture by gas chromatography showed 100% conversion of the acetone to isopropanol with 96% selectivity.

E. A glass pressure tube was charged with 40 mg of $[(Ph_3P)_2Rh]_2H^-K^+$ 3 ml of toluene and 0.5 ml of acetone. The reaction solution was pressurized to 90 psig of hydrogen and allowed to react at 90° C. for 18 hours. Analysis of the reaction mixture by gas chromatography showed 11% conversion of the acetone to isopropanol.

EXAMPLE 12

Hydrogenation of Propanal

A glass pressure tube was charged with 40 mg of the bright yellow tris-phosphine catalyst, from Example 1, $[(Ph_3P)_2(Ph_2PC_6H_4)RuH_2]^-K^+$, 1.6 gram (27.5 mmol) of propanal and 3 ml of tetrahydrofuran. The reaction solution was pressurized to 100 psi of hydrogen and allowed to react at 100° C. for 16 hours. Gas chromatographic analysis of the reaction mixture showed 80% conversion of propanal to products. The product mixture consisted of 90% by weight n-propanol and 10% by weight various other higher boiling products.

EXAMPLE 13

Hydrogenation of 1-Hexene

A glass pressure tube was charged with 40 mg of the bright yellow tris-phosphine catalyst of Example 1, $[(Ph_3P)_2(Ph_2PC_6H_4)RuH_2]^-K^+$, 0.79 gram (9.4 mmol) of 1-hexene and 5 ml of tetrahydrofuran. The reaction solution was pressurized to 10 psi of hydrogen and allowed to react at 50° C. for 5 hours. Gas chromatographic analysis of the reaction mixture showed 100% reduction to hexane. Conducting the above reaction using $[(Ph_3P)(Ph_2P)RuH]_2^-K_2^+$ as catalyst, from Example 2, produced similar results.

EXAMPLE 14

Hydrogenation of Methyl Acrylate

A glass pressure tube was charged with 40 mg of the bright yellow tris-phosphine catalyst of Example 1, $[(Ph_3P)_2(Ph_2PC_6H_4)RuH_2]^-K^+$, 0.95 gram (11 mmol) of methyl acrylate, 5 mg (0.045 mmol) of hydroquinone in a stabilizer, and 5 ml of tetrahydrofuran. The reaction solution was pressurized with 1 atmosphere of hydrogen and allowed to react at 25° C. for 20 hours. Gas chromatographic analysis of the reaction mixture showed 100% reduction to methyl propionate.

EXAMPLE 15

Hydrogenation of Acrolein

A pressure tube was charged with 40 mg of the bright yellow tris-phosphine catalyst from Example 1, $[(Ph_3P)_2(Ph_2PC_6H_4)RuH_2]^-K^+$, 20 mg of hydroquinone as a stabilizer, 1.7 gm (30.7 mmol) of acrolein and 4 ml of tetrahydrofuran. The reaction solution was pressurized with 100 psi of hydrogen and heated at 100° C. for 16 hours. Gas chromatographic analysis of the reaction mixture showed 40% conversion to products. The product mixture consisted of 75% by weight propanal, 2% by weight 1-propanol, 10% by weight allyl alcohol and 13% by weight higher boiling products. cl EXAMPLE 16

Hydrogenation of Cyclohexanone

A glass pressure tube was charged with 40 mg of the bright yellow tris-phosphine catalyst from Example 1, $[(Ph_3P)_2(Ph_2PC_6H_4)RuH_2]^-K^+$, 5 ml of tetrahydrofuran and 2 grams (20.4 mmol) of cyclohexanone. The reaction solution was pressurized to 100 psi of hydrogen and allowed to react at 80° C. for 4 hours. Gas chromatographic analysis of the reaction mixture showed the formation of cyclohexanol in 77% conversion and high selectivity (98%).

EXAMPLE 17

Hydrogenation of Benzophenone

A glass pressure tube was charged with 40 mg of the bright yellow tris-phosphine catalyst from Example 1, $[(Ph_3P)_2(Ph_2PC_6H_4)RuH_2]^-K^+$, 0.5 gram (2.74 mmol) benzophenone and 5 ml of tetrahydrofuran. The reaction solution was pressurized to 100 psi and allowed to react at 86° C. for 2 hrs. Gas chromatographic analysis of the reaction mixture showed the formation of diphenyl methanol in 15% conversion with high selectivity (98%).

EXAMPLE 18

Hydrogenation of Hexafluoroacetone

A glass pressure tube was charged with 40 mg of the bright yellow tris-phosphine catalyst from Example 1, $[(Ph_3P)_2(Ph_2PC_6H_4)RuH_2]^-K^+$, and 5 ml of tetrahydrofuran. The catalyst solution was then pressurized with 20 psi of hexafluoroacetone followed by 50 psig of hydrogen. The reaction solution was allowed to react at 50° C. for 6 hours. Gas chromatographic analysis of the reaction mixture showed 60% conversion of the hexafluoroacetone to 1,1,1,3,3,3-hexafluoroisopropanol with high selectivity (98%).

EXAMPLE 19

Hydrogenation of 2-hexyne

A glass pressure tube was charged with 20 mg of the bis-phosphine catalyst from Example 2, $[(Ph_3P)(Ph_2P)RuH]_2^-K_2^+$, 5 ml of toluene and 0.75 gram (8.9 mmol) of 2-hexyne. The reaction solution was pressurized to 90 psi of hydrogen and allowed to react at room temperature for 4 hours. Gas chromatographic analysis of the reaction mixture showed 57% conversion of the 2-hexyne to a mixture containing 68 weight percent 2-hexene and 32 weight percent n-hexane. Note: this reaction was intentionally interrupted before complete reaction occurred. It is regarded by us that different weight ratios of 2-hexene/2-hexane can be obtained by conducting the above reaction for differing time periods.

The synthesis of potassium bis(triphenylphosphine) platinum hydride was unsuccessfully attempted by us by the reaction between bistriphenylphosphine platinum hydridochloride and potassium naphthalene. However, we regard platinum as an applicable Group VIII metal in the subject compositions described herein. Basis for this is that we believe that a platinum subject composition can reasonably be prepared using the second process, i.e., reacting a Group IA metal hydride with a neutral platinum metal complex described herein.

It is believed by us on the basis of the best available evidence that the formulas of the specific compositions described herein are accurate. However, it may later be shown, for example, on the basis of neutron scattering or single crystal studies, that slight discrepancies in the given formulas may exist. However, it is believed that the actual formula will still be a species and equivalent within the scope of the general formula, as given.

We claim:

1. Anionic Group VIII metal hydride complex having 1 to 3 ligands per Group VIII metal atom, all ligands being selected from triphenyl phosphine, diphenyl phosphide, and methyldiphenylphosphine; wherein the Group VIII metal is an element selected from the first and second transition series; and the charge of the complex anion is neutralized by cations selected from Group IA and Group IIA metals.

2. The complex of claim 1 wherein M is ruthenium, rhodium or iron.

3. The complex of claim 1 having the formula:

$[(Ph_3P)_3RuH]^- K^+$, Ph being phenyl.

4. The complex of claim 1 having the formula:

$[(Ph_3P)_2RuH]^- K^+$ Ph being phenyl.

5. The complex of claim 1 having the formula:

$[(Ph_3P)(Ph_2P)Ru H]_2^- K_2^+$ Ph being phenyl.

6. The complex of claim 1 having the formula:

$[(Ph_3P)_3RhH]^- K^+$ pH being phenyl.

7. The complex of claim 1 having the formula:

$[(Ph_2P)_2Fe_2H]^= K_2^+$ Ph being phenyl.

8. The complex of claim 1 having the formula:

$[(Ph_3P)_3RuH_3]_2^- K^+$ Ph bening phenyl.

9. The complex of claim 1 having the formula:

$[(PPh_3)_2Rh]_2H^- K^+$ Ph benig phenyl.

10. The complex of claim 1 wherein said cation is complexed with a chelating agent selected from the group consisting of crown ethers and cryptates.

11. The complex of claim 1 wherein said composition is an adduct formed with an aromatic hydrocarbon.

* * * * *